United States Patent
McMullen, Jr. et al.

(10) Patent No.: US 6,241,977 B1
(45) Date of Patent: Jun. 5, 2001

(54) THERMAL PROTECTION OF HAIR KERATIN

(75) Inventors: Roger L. McMullen, Jr., Bloomfield, NJ (US); Janusz Jachowicz, Bethel, CT (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/337,995

(22) Filed: Jun. 22, 1999

(51) Int. Cl.[7] .............................. A61K 7/06; A45D 7/00; A45D 7/02
(52) U.S. Cl. .................. 424/70.1; 424/401; 132/202; 132/210; 132/211
(58) Field of Search ................... 424/401, 70.1; 132/202, 210, 211

(56) References Cited

U.S. PATENT DOCUMENTS 5,385,729 * 1/1995 Prencipe et al. .
6,048,520 * 4/2000 Hoshowski .

* cited by examiner

*Primary Examiner*—Thurman K. Page
*Assistant Examiner*—Brian K. Seidleck
(74) *Attorney, Agent, or Firm*—Walter Katz; William J. Davis; Marilyn J. Maue

(57) ABSTRACT

A method of protecting hair or wool against thermal degradation when heat treated at 100–180° C. which comprises applying a composition which includes methyl vinyl ether-maleic acid copolymer as an active constituent to said hair or wool.

4 Claims, 11 Drawing Sheets

MVE/Maleic Acid Copolymer
Gantrez S97 BF-MW=2,000,000
ACV 4043

FIG. 11

THERMAL PROTECTION OF HAIR KERATIN

BACKGROUND OF THE INVENTION

1. Field of the Invention

This invention relates to thermal degradation of hair, and, more particularly, to a method of protecting hair against such degradation when heat treated with thermal styling appliances to impart desirable styling characteristics to the hair.

2. Description of the Prior Art

Several commercial products are available to protect hair from heat styling appliances. These products often contain a wide range of actives including hydrolyzed proteins, enzyme cofactors, fatty acids, saccharides, surfactants, and various polymers. Hydrolyzed wheat protein, wheat oligosaccharides, wheat amino acids, and panthenol, when formulated together, are believed to increase the strength and moisture retention of hair fibers when used in conjunction with a thermal styling appliance. Additionally, the thermal protection properties of PVP and panthenol have been investigated outside of a formulation. Several patents specifically identify a compound or formulation as a thermal protector against hair dryers or hot irons. For hair dryer protection, the following systems were prescribed: high molecular weight silicone and fatty acid alkanol amides; mono-N-acyl basic amino acid lower alkyl ester salt and/or cationic surfactant, liquid oil, and heme iron compound; quaternary ammonium salts, one or a mixture of crude extract from the rind of fruits, and a water-soluble polymers having a quaternary nitrogens; and a conditioner containing stearyltrimethyl-ammonium chloride and polyethylene-polypropylene glycol butyl ether as its actives. There are also patents that strictly relate to protecting hair from hot irons. One formulation includes a two-phase system and a surfactant. The oil phase consists of one or a mixture of ester oils, triglycerides, higher alcohols, animal oils, plant oils, and silicone oils while the aqueous phase contains glycerol, propylene glycol, and polyethylene glycol. The surfactant may be nonionic, cationic, or anionic. Another composition, consisting of polyoxyethylene sorbitol tetraoleate, polyoxyethylene castor oils, fatty acids (from animal or vegetable sources), and a nonionic surfactant, has also been suggested to protect hair from hot irons.

Several compounds have been used as thermal setting agents, in which the active is applied to hair prior to or during thermal treatment. Specifically, the application of a thermoplastic polyester fixative resin used in conjunction with a thermal styling appliance has been described in the patent literature. Similar to hair fibers, cotton fibers may experience similar interactions with compounds when subjected to high temperatures. The cross-linking of cellulose with polycarboxylic acids has received a significant amount of attention within the textile industry as an alternative method for permanent pressing finished cotton fabrics.

The thermal yellowing of wool, and its prevention, represents another important problem within the textile industry. Although the mechanism of wool thermal yellowing and its prevention are not fully understood, several compounds have been identified as inhibitors of yellowing. Most significantly, maleic anhydride was found to retard wool thermal yellowing to a significant degree. A similar effect was observed when wool was immersed in dilute $H_2SO_4$ prior to thermal exposure. Overall, evidence indicates that the yellowing of wool is pH sensitive, with the degree of yellowing increasing with increasing pH.

Accordingly, it is an object of this invention to provide a method of protecting hair or wool against thermal degradation when heat treated at elevated temperatures.

A feature of the invention is the application of a composition of methyl vinyl ether-maleic acid copolymer, to protect hair or wool against thermal degradation when heat treated at 100–180° C.

SUMMARY OF THE INVENTION

A method of protecting hair or wool against thermal degradation when heat treated at 100–180° C., preferably 130–160° C. comprises applying a composition which includes methyl vinyl ether-maleic acid copolymer as an active constituent to the hair or wool.

DESCRIPTION OF THE INVENTION

This invention is hereinafter described with reference to preferred embodiments wherein hair or wool is protected against thermal degradation. The invention also finds utility in protecting other natural fibers, such as cotton, and synthetic fibers from thermal degradation.

Experimental

Instrumentation

The instrumentation used to quantify thermally induced changes in hair structure has been described by R. McMullen et al, J. Cosmet. Sci., 49, 223–244 (1998). Additionally, experiments in which the mechanical properties of the polymer or surfactant treated thermally exposed fiber assembly could be quantified. This was achieved utilizing a texture analyzer (Model TA-XT2), from Texture Technologies Corp., along with several additional features enabling us to perform dual cantilever bending experiments.

The texture analyzer had a load sensitivity of 0.1 g and was operated using XTRA dimension software 3.7 from Stable Micro Systems.

The analysis of fiber assembly stiffness represents the primary mechanical measurement obtained using the texture analyzer in conjunction with the cantilever bending assembly (CBA). The CBA in which the hair tress rests on the cantilevers, and the modified probe, which is attached to the texture analyzer, creates a deformation in the hair tress. For the measurements, the tress was fastened to a clamp. During each test, the modified probe would penetrate the hair sample until it sensed a 2.0 G force, pierce 3.0 mm into the fiber assembly, return to the position where the load cell initially detected the 2.0 G force, remain at this position for 3 seconds, and penetrate the sample again to make a second deformation, also 3.0 mm. The force required to generate the 3 mm deformation represents the actual stiffness of the fiber assembly.

Materials & Methods

The thermal treatment of hair was performed using a Soft Sheen, Optimum Styling Tools, Curling Iron (Model SOC125S) manufactured by Continental Hair Products, Glendale, Ariz., USA. As indicated by McMullen et al cited above, thermal treatment to each hair tress was administered in the same position in order to maintain experimental uniformity. Unless otherwise indicated, thermal treatment in the majority of experiments was administered for a duration of 1 min. The sum of all heating cycles constitutes a total treatment time, normally 10 min in duration. After each 2 min interval, the samples were thoroughly rinsed followed by combing measurements. After combing, the samples were saturated with $H_2O$ and the excess was removed from the hair tress by squeezing and sliding the index and middle finger down the length of the tress. This provided each sample with a defined geometry in the moist state at which point the samples were allowed to stand overnight at 50% RH. We were then able to perform stiffness measurements using the texture analyzer. After 1 shampooing, the samples were again subjected to combing analysis followed by the process described above prior to texture analysis. Once the mechanical measurements were completed, we obtained fluorescence spectra and tristimulus (L, a, b) values from the spectrocolorimeter in order to monitor the tryptophan (Trp) degradation and the color changes induced by the thermal treatments. For each color and fluorescence measurement, readings were obtained from the thermally exposed and unexposed positions of the hair tress.

The hair tress treatments were administered with 1% solutions of the indicated active. The fibers were saturated with $H_2O$ prior to treatment, followed by towel drying, leaving some added $H_2O$ in the fiber assembly. The damp hair was saturated with the active (2.5 g), followed by removal of any excess treatment, then towel dried. This resulted in a 0.55 g application of the 1% active (3.46 mg of Active/1 g of hair). The treated tress was then air-dried (23.3° C.) with an Elchim Professional hair dryer (model EC 35227), distributed by Elchim—USA, Inc., 735 Rahway Avenue, Union, N.J. After drying, the hair tresses were subjected to thermal treatment as described above. Experiments were performed on Light Brown Hair purchased from International Hair Importers & Products, Inc., Valhalla, N.Y. Additionally, Piedmont hair, purchased from DeMeo Brothers, Inc., New York, N.Y., was used to gain a better understanding of the mechanism of thermally induced yellowing.

Polymers & Surfactants

Methyl Vinyl Ether/Maleic Acid Copolymer is a commercial product sold under the trade names of Gantrez S97 and Gantrez 4043 by International Specialty Products, Inc., Wayne, N.J. Sodium Bisulfite (Aldrich Chemical Co., Inc., Milwaukee, Wis.) was used for studies on Piedmont hair, in which the degree of yellowing could be monitored. The pH of Sodium Bisulfite, MVE/MA Copolymer (Gantrez S97 and Gantrez 4043) was adjusted with 2-Amino-2-Methyl-1-Propanol purchased from Angus Chemical Copany, Buffalo Grove, Ill.

Results & Discussion

Spectroscopic Analysis

The decomposition of Trp in thermally exposed fibers was investigated for a series of polymers and surfactants. Primarily, the experiments were performed at temperatures of 132° C. and 152° C. and for heating periods of 1 min constituting a total heating time of 10 min or 12 min. We also explored other temperatures and treatment periods.

Figure 1:
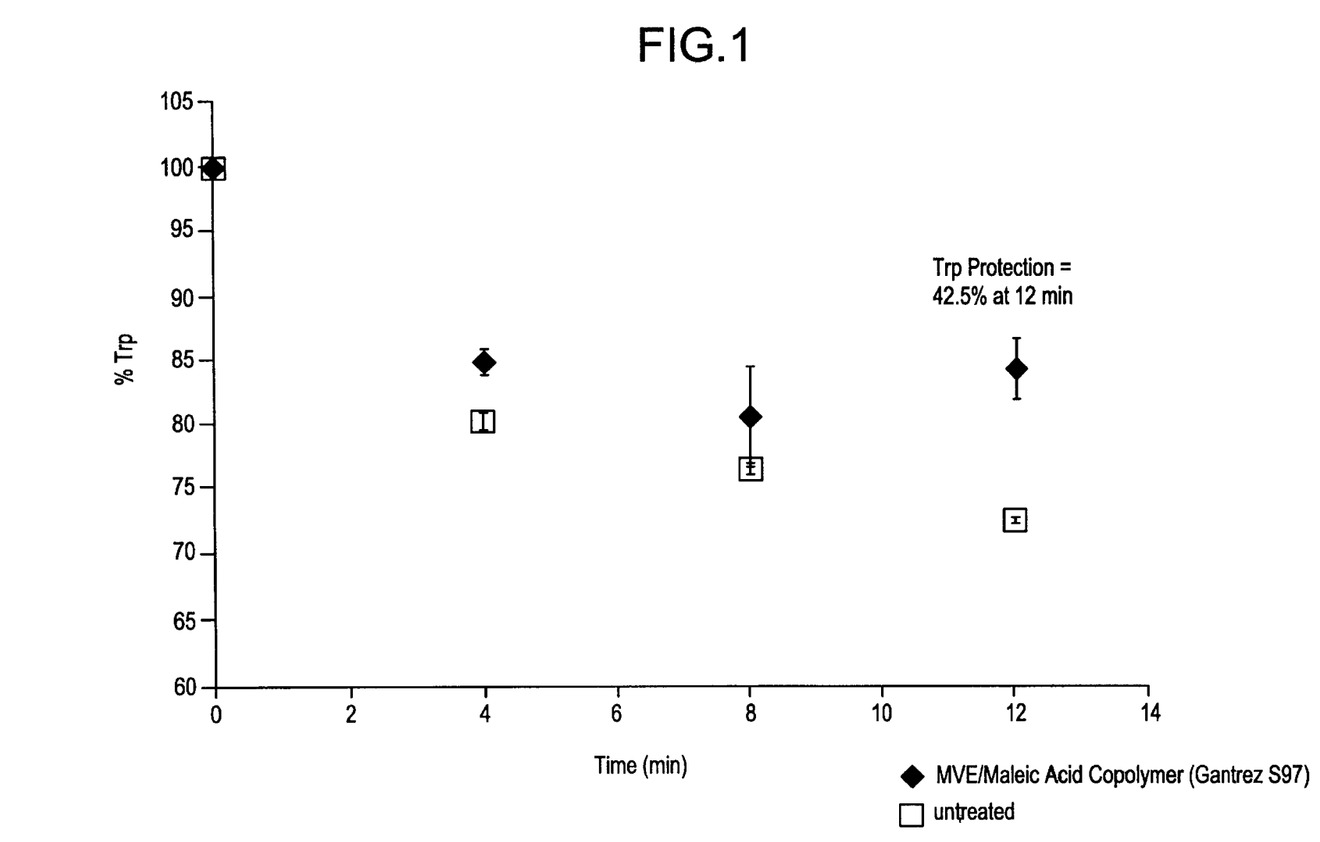
FIG. 1 Effect of Methyl Vinyl Ether/Maleic Acid Copolymer (Gantrez S97) on tryptophan thermal degradation in light brown hair at 132° C.
Figure 2:
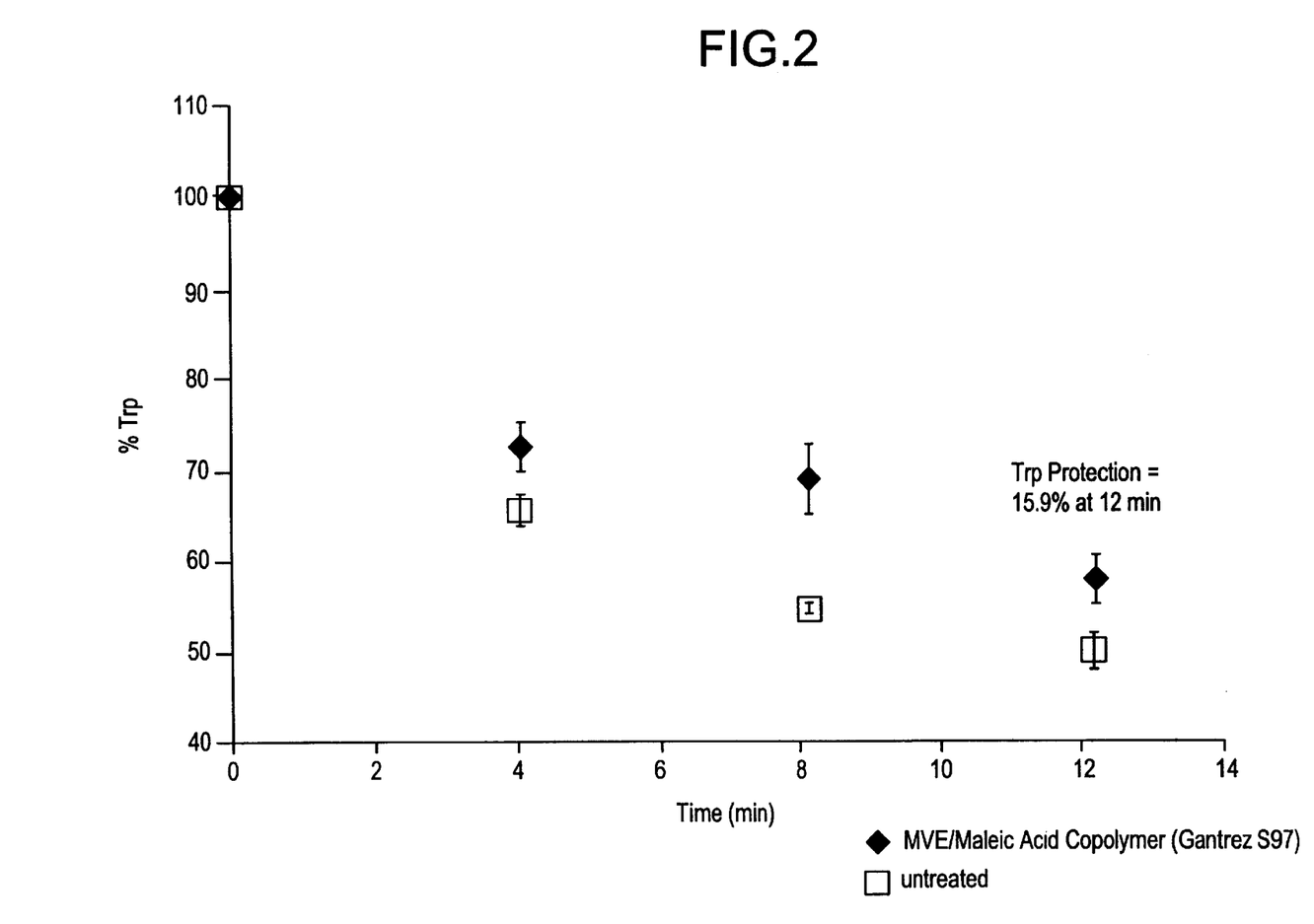
FIG. 2 Effect of Methyl Vinyl Ether/Maleic Acid Copolymer (Gantrez S97) on tryptophan thermal degradation in light brown hair at 152° C.

Our findings suggest that Trp decomposition, due to thermal exposure, can be impeded using several of the tested polymers and surfactants. In both Piedmont and Light Brown hair, MVE/MA copolymer appears to provide the most substantial degree of Trp protection at temperatures of 132° C. and 152° C. FIG. 1 demonstrates the progression of Trp damage as a function of thermal treatment time for untreated samples and for samples treated with MVE/MA copolymer. The data presented were obtained from tests on light brown hair that was exposed to a curling iron temperature of 132° C. The data indicate that treatment with the tested polymers or surfactants results in an increase in Trp level when compared to untreated hair. Additionally, FIG. 2 presents the percent Trp as a function of the thermal treatment time for light brown hair treated with the indicated compounds and subjected to a curling iron temperature of 152° C. At both temperatures, the data were recorded every 4 min after 4 subsequent treatment and curling iron exposure intervals of 1 min. At both temperatures, the Trp level is highest for hair treated with MVE/MA Copolymer (Gantrez S97).

Figure 3:
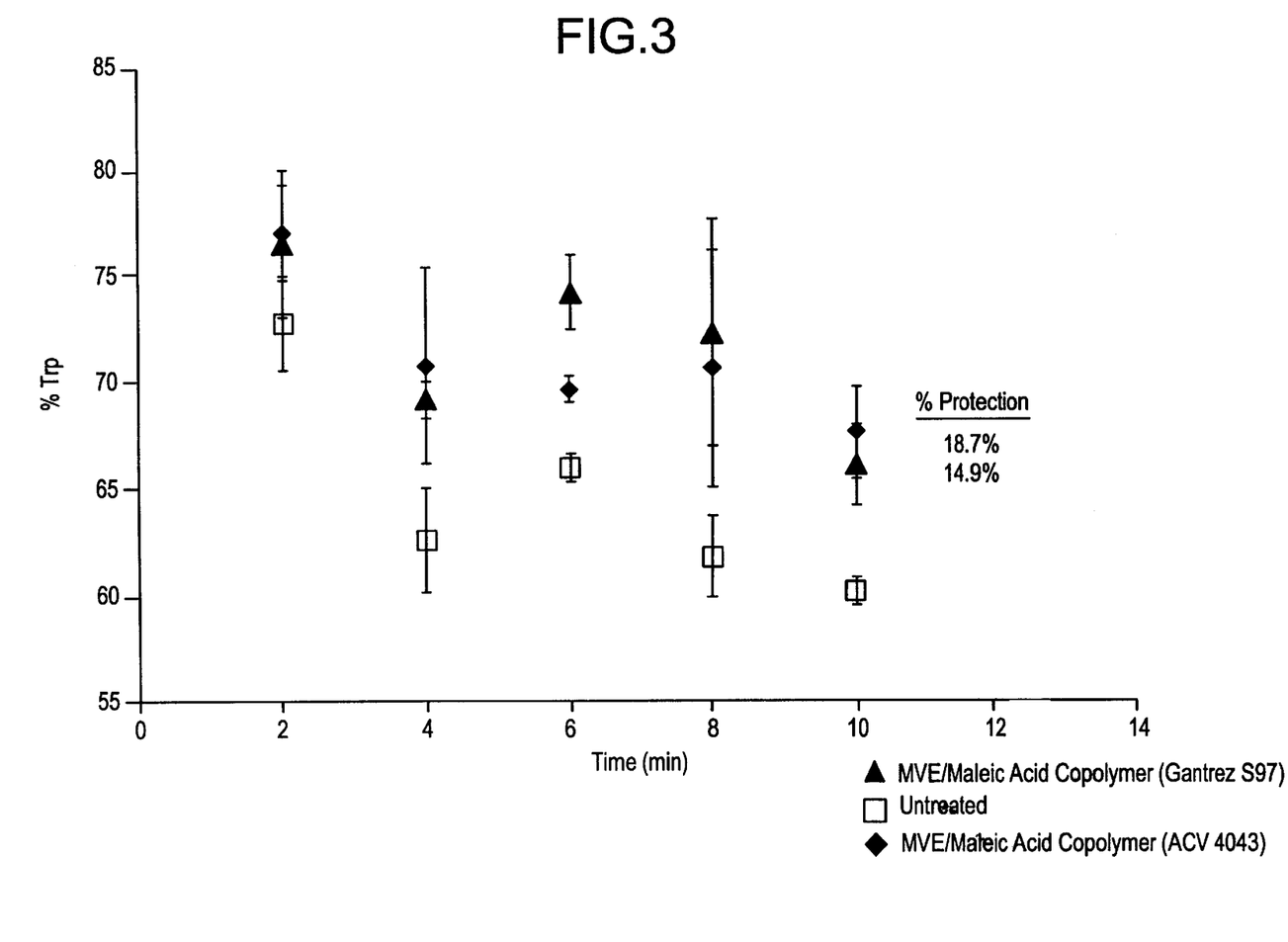
FIG. 3 Effect of Methyl Vinyl Ether/Maleic Acid Copolymers (Gantrez S97 and ACV 4043) on tryptophan thermal degradation in Piedmont hair at 132° C.
Figure 4:
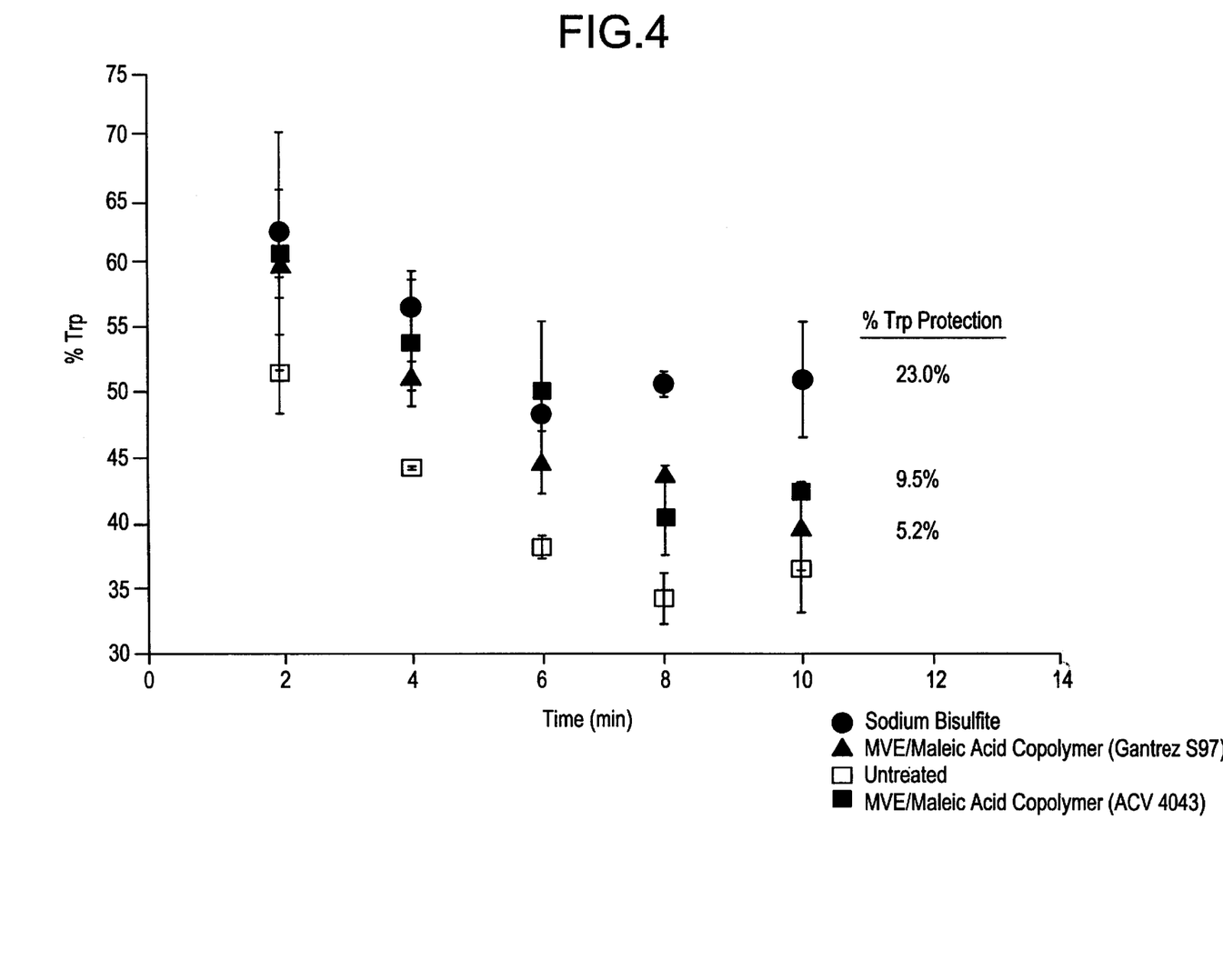
FIG. 4 Effect of Methyl Vinyl Ether/Maleic Acid Copolymers (Gantrez S97 and ACV 4043) on tryptophan thermal degradation in Piedmont hair at 152° C.

In our investigations with Piedmont hair, we found that MVE/MA Copolymer provided the same effect, as with Light Brown hair, when exposed to temperatures of 132° C. and 152° C. Similarly, we found that MVE/MA copolymer (Gantrez 4043) also provided thermal protection for Piedmont hair. FIG. 3 illustrates the thermal decomposition of Trp at 132° C. for untreated and MVE/MA Copolymer (Gantrez S97 and Gantrez 4043) treated hair. Sodium Bisulfite also provided a reduction in the Trp degradation. As shown in FIG. 4, after 10 min of thermal exposure at 152° C., Sodium Bisulfite treated hair contained 51.07% Trp as compared to untreated hair in which only 36.37% Trp remained. It has been well established that MVE/MA Copolymer, in its hydrated form, will become anhydrous upon heating (i.e., >125° C.). As a result, $H_2O$ will evolve in the course of the reaction. The large heat of evaporation ($\Delta H_{vap}$) for $H_2O$ may be a plausible explanation for the additional Trp protective effect when MVE/MA Copolymer is applied to hair. We have demonstrated that $H_2O$, alone, does in fact provide a substantial degree of protection to Trp in hair fibers.

We also examined the Trp decomposition after altering the pH of the tested compounds. MVE/MA Copolymer (Gantrez 4043) was prepared as a 1% solution, with no neutralization, resulting in a pH of 2.4. Another solution of MVE/MA Copolymer (Gantrez 4043) was neutralized with 2-amino-2-methyl-1-propanol to pH 3.4. Similarly, Sodium Bisulfite was tested, without neutralization, at pH 2.9. Additionally, another test sample of Sodium Bisulfite was prepared and neutralized with 2-amino-2-methylpropanol to pH 4.1. For Sodium Bisulfite, the change in pH did not effect its Trp protecting capabilities. After 10 min of thermal treatment, with 1 min intervals, Sodium Bisulfite treated hair contained 51.07% +4.53% Trp at pH 4.1 and 51.58%±1.57% Trp at pH 2.9. However, MVE/MA copolymer (Gantrez 4043) provided a more distinguishable difference when the pH was altered. Again, after 10 min of thermal treatment, MVE/MA Copolymer (Gantrez 4043) treated hair contained 42.42%±0.06% Trp at pH 3.4 and 49.1%±2.36% at pH 2.4.

Combing Analysis

In an attempt to observe the surface modification induced by polymers and surfactants when used in conjunction with thermal treatment, we performed combing analysis of all samples. Our findings suggest that at high temperatures a myriad of possible chemistries may be occurring when an active is placed on hair prior to thermal exposure. Most notably, we see an increased affinity to hair in the case of MVE/MA Copolymer (Gantrez S97 and Gantrez 4043).

Figure 5:
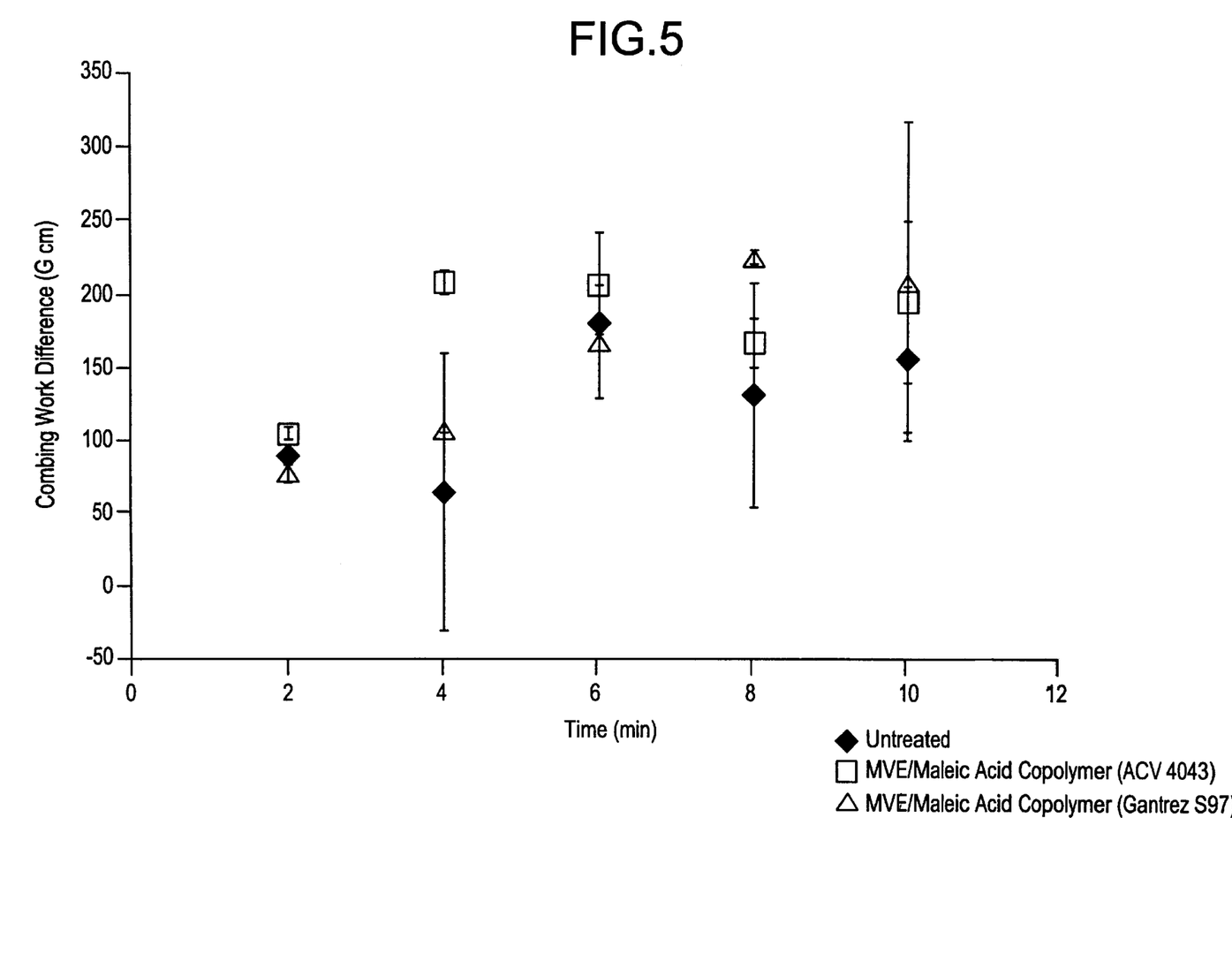
FIG. 5 Effect of Methyl Vinyl Ether/Maleic Acid Copolymers (Gantrez S97 and ACV 4043) on the combing work of Piedmont hair after thermal treatment at 132° C.
Figure 6:
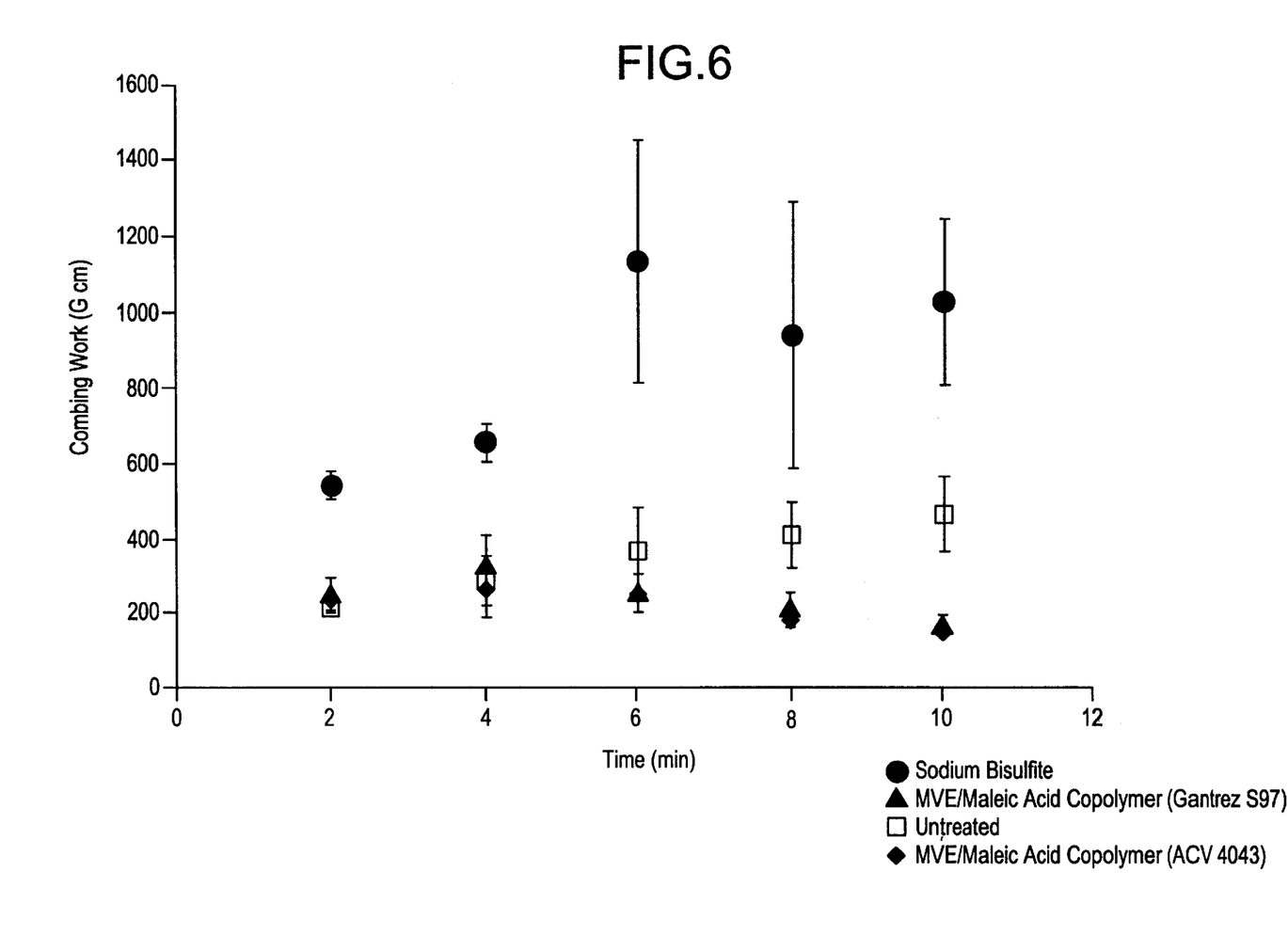
FIG. 6 Effect of Methyl Vinyl Ether/Maleic Acid Copolymers (Gantrez S97 and ACV 4043) on the combing work of Piedmont hair after thermal treatment at 152° C.
Figure 7:
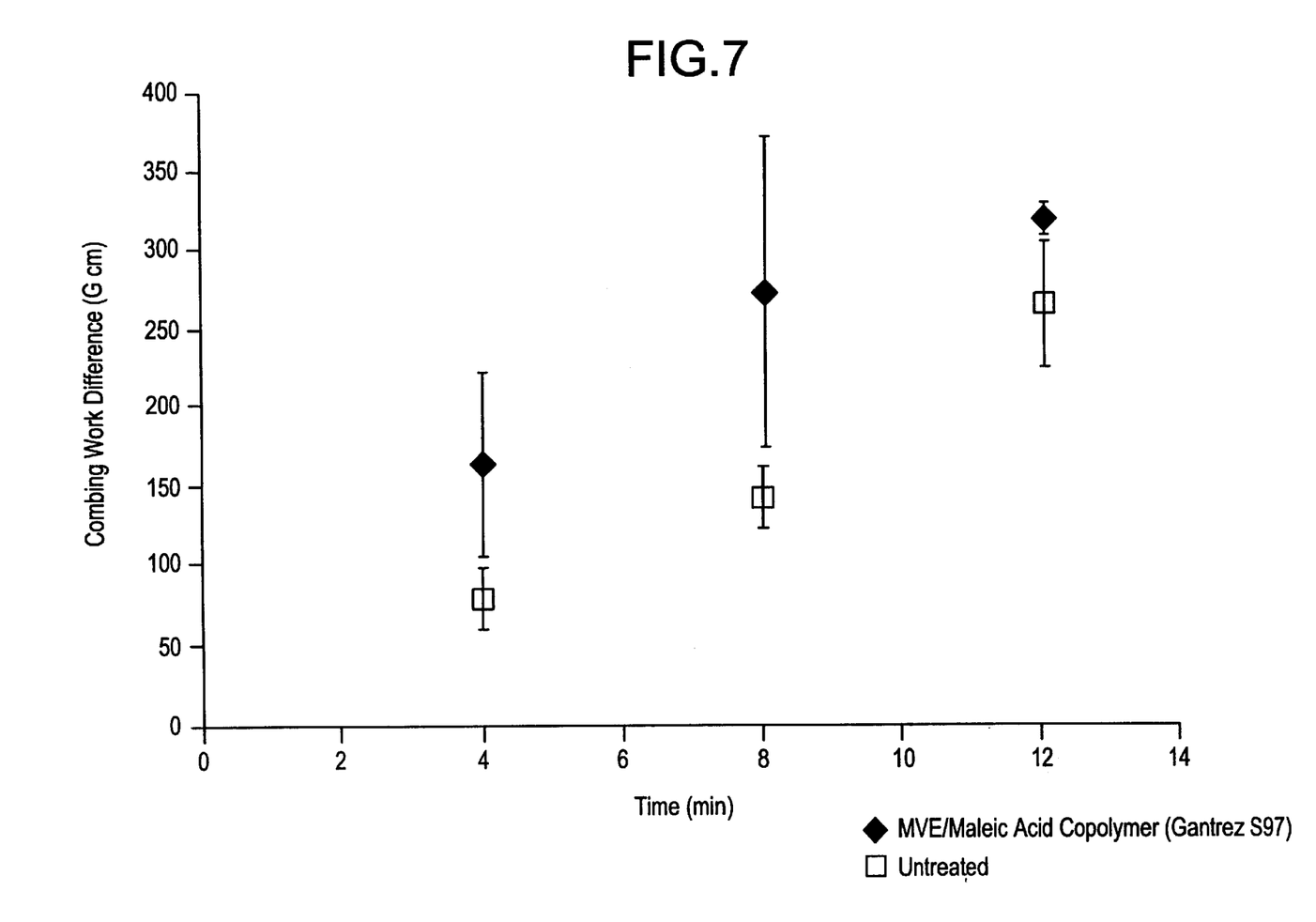
FIG. 7 Effect of Methyl Vinyl Ether/Maleic Acid Copolymer (Gantrez S97) on the combing work of light brown Caucasian hair after thermal treatment at 132° C.
Figure 8:
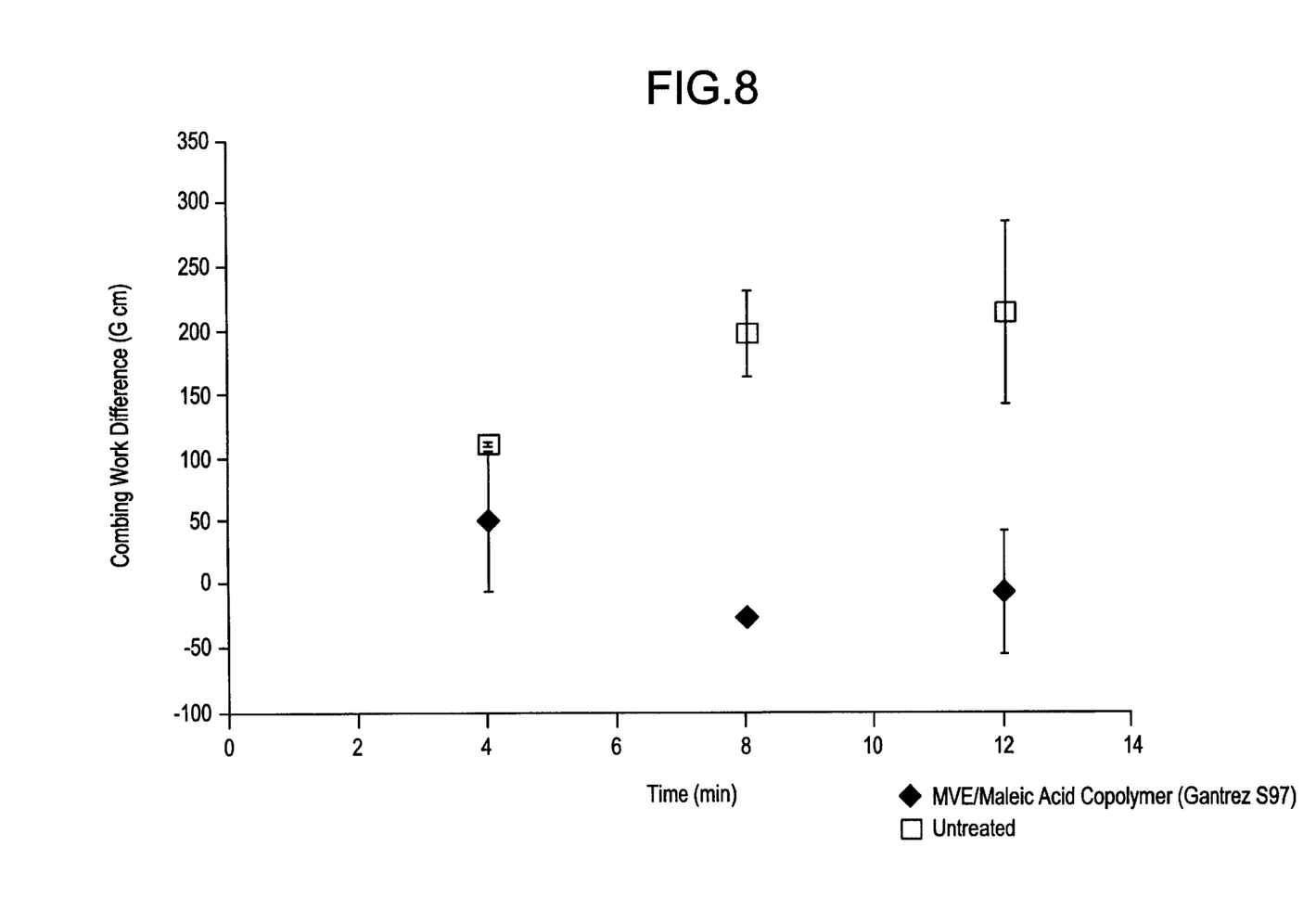
FIG. 8 Effect of Methyl Vinyl Ether/Maleic Acid Copolymer (Gantrez S97) on the combing work of light brown Caucasian hair after thermal treatment at 152° C.

We have found that untreated hair experiences an increase in the fiber frictional properties, which we attribute to delipidization of the fiber surface. This is represented by the increase we report for combing work difference. A detailed explanation for the determination of combing work difference is provided by McMullen et al cited above. FIGS. 5 and 6 present combing work difference as a function of time at 132° C. and 152° C., respectively. As indicated in FIG. 5, hair treated with Methyl Vinyl Ether/Maleic Acid Copolymer (Gantrez S97) and subjected to a curling iron temperature of 132° C. is slightly more difficult to comb than untreated light brown hair. However, when exposed to a curling iron temperature of 152° C., Methyl Vinyl Ether/Maleic Acid Copolymer (Gantrez S97) is much easier to comb than untreated hair. The combing data in FIGS. 5 and 6 were obtained after shampooing and each 4 min heating cycle consisting of 1 min intervals. We also obtained similar data for Piedmont hair, which is included in FIGS. 7 and 8. FIG. 7 provides the combing work difference values for Piedmont hair treated with Methyl Vinyl Ether/Maleic Acid Copolymer (Gantrez S97), Methyl Vinyl Ether/Maleic Acid Copolymer (Gantrez 4043), and for untreated Piedmont hair subjected to a curling iron temperature of 132° C. Again, exposure at 1320C results in combing work difference values in which hair treated with Methyl Vinyl Ether/Maleic Acid Copolymer slightly more difficult to comb than untreated hair. However, at 152° C. (FIG. 8) thermally exposed hair treated with Methyl Vinyl Ether/Maleic Acid Copolymer is much easier to comb than untreated hair. FIG. 8 also contains the values of combing work difference for thermally exposed hair treated with Sodium Bisulfite, which demonstrates that this compound damages the hair surface and produces a significant increase in combing forces.

In summary, use of Methyl Vinyl Ether/Maleic Acid Copolymer (Gantrez S97 or Gantrez 4043) in conjunction with thermal treatment resulted in a reduction in combing work at 152° C. for both types of hair. However, at 132° C. we observed an increase in combing forces, even more so than untreated hair. Aside from the different behavioral characteristics of Methyl Vinyl Ether/Maleic Acid Copolymer, the only difference in operating at the two temperatures was the magnitude of the combing forces. As expected, at 132° C. the surface modification was less pronounced than at 152° C.

Textural Properties

Throughout the course of our experiments, we observed that the mechanical properties of the hair fiber assemblies could change when certain polymers were used in conjunction with thermal treatment. The most predominant case was that for MVE/MA Copolymer, which we attribute to cross-linking of the polymer with hair keratin. By visual inspection and the use of texture analysis we were able to identify and quantify a stiffening effect.

Figure 9:
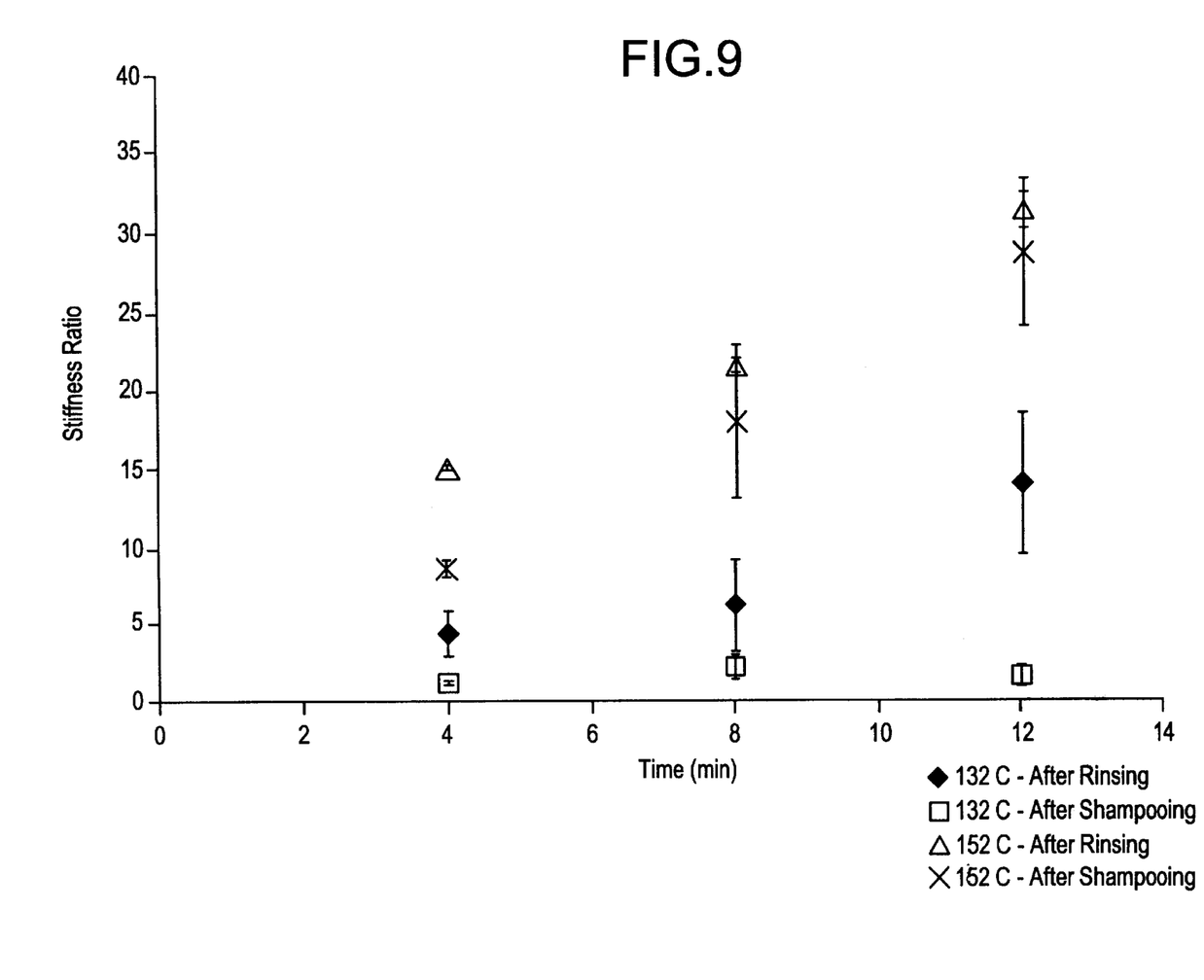
FIG. 9 Effect of Methyl Vinyl Ether/Maleic Acid Copolymer (Gantrez S97) on the stiffness of light brown Caucasian hair tresses after thermal treatment at 132° C. and 152° C. followed by rinsing or shampooing.
Figure 10:
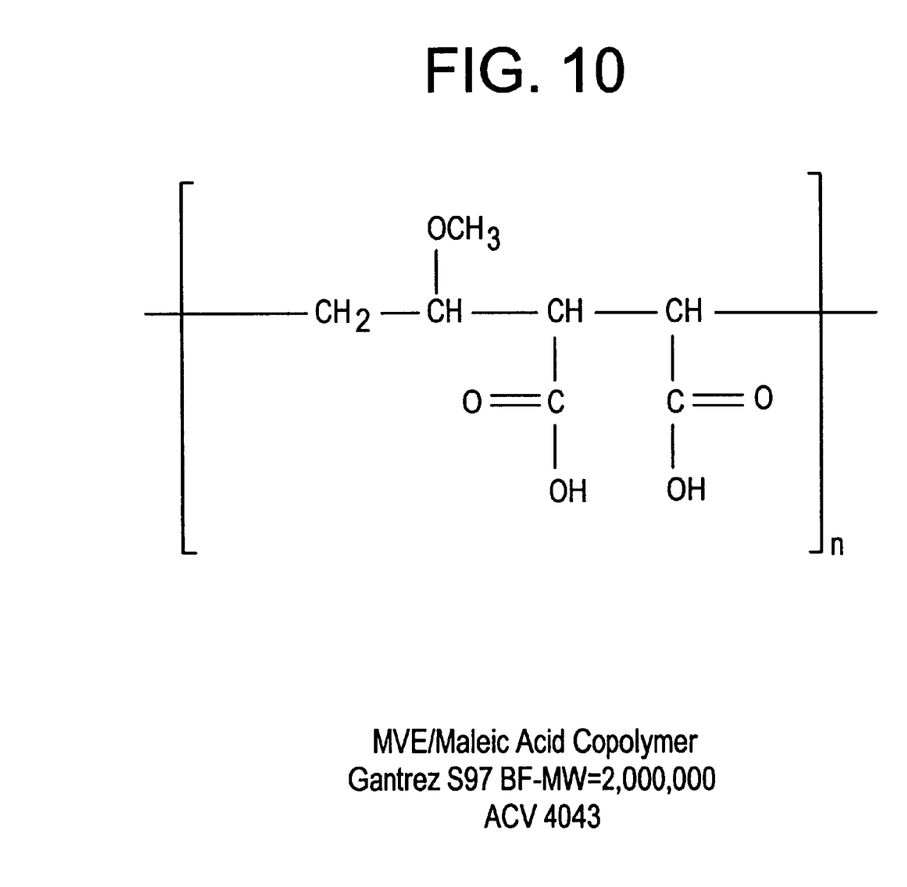
FIG. 10 Structure of Methyl Vinyl Ether/Maleic Acid (MVE/MA) Copolymers

We administered textural profile analyses on all of the samples that had been subjected thermal exposure. This analysis consisted of determining stiffness, resilience, and springiness. Stiffness was the only parameter that changed when comparing the heat-treated hair to its initial state. The only pronounced effect was produced by MVE/MA Copolymer (Gantrez S97). FIG. 9 presents stiffness ratio as a function of time for hair treated with MVE/MA Copolymer and subjected to 12 min of curling iron application. Stiffness ratio represents the ratio of stiffness in grams after treatment and heat application to the corresponding stiffness before treatment. As indicated by FIG. 9, the stiffness of the fiber assembly increases as the heating time and treatment cycles increases. We recorded the stiffness of the fibers after the hair was rinsed, and after subsequent shampooing, in order to illustrate the substantivity of MVE/MA Copolymer (Gantrez S97) to the keratin fibers.

Figure 11:
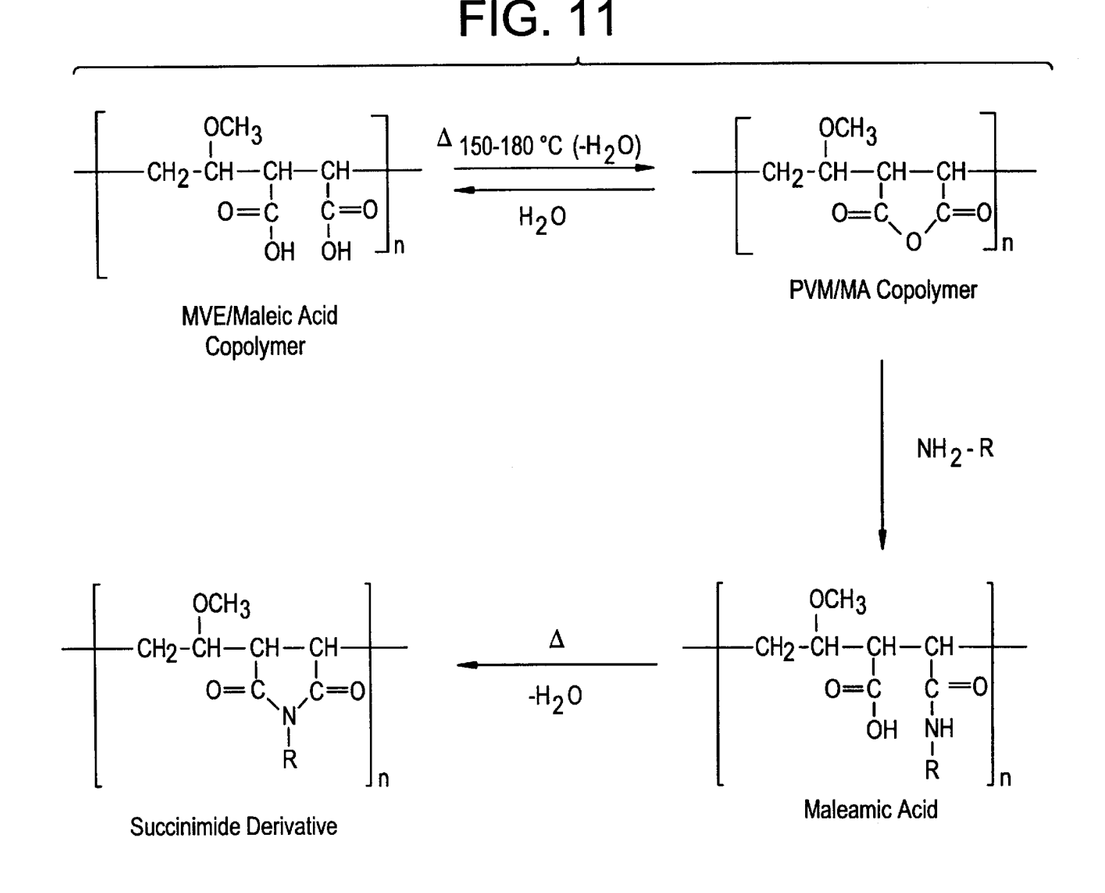
FIG. 11 Chemical reactions illustrating high temperature dehydration of Methyl Vinyl Ether/Maleic Acid Copolymer and the formation of imide.

In attempt to provide an explanation for the change in textural properties of MVE/MA Copolymer (Gantrez S97) treated hair, we have relied on some fundamental concepts in maleic anhydride chemistry. FIG. 11 offers a plausible explanation for the cross-linking of MVE/MA to keratin fibers As illustrated by FIG. 11, upon heating the hydrated form of MVE/MA Copolymer will become anhydrous resulting in the evolution of $H_2O$. Continual heating in the presence of an amine will result in the formation of a cyclic imide.

While the invention has been described with particular reference to certain embodiments thereof, it will be understood that changes and modifications may be made which are within the skill of the art. Accordingly, it is intended to be bound only by the following claims.

What is claimed is:

1. A method of protecting hair or wool against thermal degradation when heat treated at 100–180° C. which comprises applying a composition which includes about 2–20 mg/g of hair of methyl vinyl ether-maleic acid copolymer having the formula as an active constituent to said hair or wool before heating.

2. The method according to claim 1 wherein said composition is applied in the presence of water.

3. The method according to claim 1 wherein said active is applied to hair.

4. The method according to claim 1 wherein said temperature is 130–160° C.

* * * * *